(12) United States Patent
Wates et al.

(10) Patent No.: US 6,494,944 B1
(45) Date of Patent: Dec. 17, 2002

(54) AMINE OXIDES AS ASPHALT EMULSIFIERS

(75) Inventors: Julia Mary Wates, Chicago, IL (US); Bengt-Arne Thorstensson, Alta (SE); Alan James, Naperville, IL (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/517,478

(22) Filed: Mar. 2, 2000

(51) Int. Cl.$^7$ .......................... B01F 17/16; C08L 95/00
(52) U.S. Cl. ......................................... 106/277; 516/43
(58) Field of Search ............................. 516/43; 106/277

(56) References Cited

U.S. PATENT DOCUMENTS

| | | | | |
|---|---|---|---|---|
| 2,690,978 A | | 10/1954 | Cross | 106/277 |
| 3,126,350 A | * | 3/1964 | Borgfeldt | 516/43 |
| 3,422,026 A | * | 1/1969 | Wright | 516/43 X |
| 3,513,005 A | | 5/1970 | Bradshaw et al. | 106/277 |
| 3,539,368 A | | 11/1970 | Timmons et al. | 106/277 |
| 3,957,524 A | * | 5/1976 | Doughty et al. | 516/43 X |
| 4,146,499 A | | 3/1979 | Rosano | 252/186 |
| 4,395,373 A | | 7/1983 | Login et al. | 260/928 |
| 4,419,140 A | | 12/1983 | Richmond et al. | 106/273 N |
| 4,869,804 A | | 9/1989 | Le Perchec et al. | 208/106 |
| 5,098,604 A | * | 3/1992 | Brouard et al. | 106/277 X |

FOREIGN PATENT DOCUMENTS

| | | | |
|---|---|---|---|
| DE | 1 719 449 | 10/1972 | ........... B01F/17/16 |
| EP | 0 037 996 | 10/1981 | ......... C07C/135/02 |
| GB | 1 104 491 | 2/1968 | ......... C07C/135/00 |
| JP | 8-3573 | 1/1996 | ............. C10L/1/32 |
| JP | 8-73873 | 3/1996 | ............. C10L/1/32 |
| JP | 114400 | 4/1999 | ........... B01F/17/22 |
| WO | 94/03560 | 2/1994 | ............. C10L/1/32 |
| WO | 97/11993 | 4/1997 | ............. C08K/5/32 |

OTHER PUBLICATIONS

*Chemical Abstract*, 115186618, dated Apr. 23, 1991.
*Chemical Abstract*, 115186617, dated Apr. 23, 1991.
*Chemical Abstract*, 115186616, dated Apr. 23, 1991.
*Chemical Abstract*, 105136912, dated Jun. 10, 1986.
*Chemical Abstract*, 104023472, dated Jun. 27, 1985.
*Chemical Abstract*, 93012378, dated Sep. 13, 1979.
*Chemical Abstract*, 86018107, dated Sep. 14, 1976.
*Chemical Abstract*, 78163397, dated 1972.
*Chemical Abstract*, 74034318, dated Nov. 10, 1970.
*World Patent Index Chemical Abstract*, 002251712, dated Mar. 6, 1978.
*World Patent Index Chemical Abstract*, 002207642, dated May 19, 1977.
*World Patent Index Chemical Abstract*, 000911084, dated Sep. 14, 1967.
*World Patent Index Chemical Abstract*, 000682946, dated Sep. 18, 1968.
*World Patent Index Chemical Abstract*, 000588278, dated Oct. 24, 1966.
*World Patent Index Chemical Abstract*, 000551509, dated Jul. 22, 1965.
*World Patent Index Chemical Abstract*, 007052081, dated Aug. 6, 1985.
*World Patent Index Chemical Abstract*, 004333219, dated Dec. 17, 1983.
*World Patent Index Chemical Abstract*, 003219478, dated Apr. 16, 1980.
*World Patent Index Chemical Abstract*, 003214546, dated Mar. 26, 1979.
*World Patent Index Chemical Abstract*, 000686376, dated Dec. 13, 1967.
*Derwent Abstract*, 094506, dated 1996 for JP08003573.
*Derwent Abstract*, 205835, dated 1996 for JP08073873.
*Abstract*, 72–71253T for DE1719449 dated Oct. 26, 1972.
*Derwent Abstract*, 80036 D/44, dated Oct. 21, 1981 for EP 0 037 996.
*Derwent Abstract*, 94–065655/08, dated Feb. 17, 1994 for WO 94/03560.
*Japanese Patent Office Abstract*, 265761, dated Apr. 27, 1999.
Kinetics and Preparation of Amine Oxides, C. J. Toney, et al., *JAOCS*, vol. 71, No. 7, Jul. 1994.
*Patent Abstracts of Japan* 11279410, dated Oct. 12, 1999.
*Patent Abstracts of Japan* 2000178532, dated Jun. 27, 2000.
*Patent Abstracts of Japan* 06100872, dated Apr. 12, 1994.
International Search Report PCT/IB 01/00460, dated Oct. 5, 2001.
Written Opinion of International Application No. PCT/IB01/00460 dated Nov. 23, 2001.

* cited by examiner

*Primary Examiner*—Richard D. Lovering
(74) *Attorney, Agent, or Firm*—Lainie E. Parker

(57) ABSTRACT

A method of emulsifying asphalt using a polyamine polyoxide, preferably a diamine dioxide, as an emulsifier or co-emulsifier and an emulsion of asphalt, water and a polyamine polyoxide, preferably a diamine dioxide. The advantages of using a polyamine polyoxide as an emulsifier or co-emulsifier include its ability to provide superior cationic and anionic emulsions, and slow-setting emulsions at low use levels, and the excellent adhesion of the cured asphalt film.

30 Claims, No Drawings

AMINE OXIDES AS ASPHALT EMULSIFIERS

FIELD OF THE INVENTION

The present invention generally relates to the use of polyamine polyoxides as asphalt emulsifiers. More particularly, the invention concerns an improved process for stabilizing an asphalt in water emulsion using a di-tertiary amine dioxide as an asphalt emulsifier.

BACKGROUND OF THE INVENTION

Asphalt in water emulsions are used for road construction and repair, as well as in the construction industry as coatings and sealers. The asphalt properties are obtained after the emulsions set or cure, when the droplets of asphalt coalesce and adhere to the substrate and water is removed.

The rate of this setting process depends on the reactivity of the emulsion and the reactivity of the substrate. Emulsions are classified as rapid, medium and slow-setting types depending on their reactivity. Slow-setting emulsions find use in applications, such as cold mix, where the emulsion is mixed with aggregate and the mixture is used to pave a roadway.

Emulsions can be classified into cationic (positive) or anionic (negative) types depending on the charge on the asphalt droplets. Cationic emulsions are used for siliceous aggregates, like quartz, since such aggregates have negatively charged surfaces. The cured film from cationic emulsions generally adheres much better to siliceous aggregates than does the cured film from anionic emulsions. Generally, different emulsifiers are used for cationic emulsions than are used for anionic emulsions.

Nonionic emulsifiers, such as ethoxylated nonylphenols, can be used as part of an emulsifier or alone in both cationic and anionic slow-setting emulsions. However, at use levels comparable to the inventive emulsifier, the anionic and cationic slow-setting emulsions of ethoxylated nonylphenols are deficient in quality. Additionally, films of asphalt derived from such emulsions tend to strip off the aggregate when soaked in water.

Amine monoxides, such as $RN(CH_3)_2O$, $RCONCH_2CH_2CH_2N(CH_3)_2O$ (an amide amine oxide) or $RN(CH_2CH_2OH)_2O$, where R is a $C_{12}$ alkyl, coconut oil or tallow, have some efficacy as cationic asphalt emulsifiers. However, they generally cannot be used to produce both anionic and cationic emulsions. When they can form both anionic and cationic emulsions, the quality of the emulsions is deficient and they do not meet the requirements of slow-setting emulsions at economic use levels. Instead, they form rapid- or medium-setting emulsions which cannot be used with reactive aggregates.

The use of amine oxides as asphalt emulsifiers has been disclosed. For example, DE 1 719 449 (DE'449) discloses the use of tertiary amine oxides as a bitumen emulsion additive which is combined with a cationic emulsifier for road surfacing, while WO 94/03560 discloses the use of amine oxides as a cationic surfactant in asphalt/bitumen emulsions. Additionally, EP 0 037 996 discloses the use of an amine oxide with a napthenoyl group for emulsifying bituminous products. These amide amine oxides would have the same problems as the amine oxides discussed above.

A di-tert-amine dioxide comprising (hydrogenated) tallow groups is disclosed for use as a detergent or as an emulsifier of, for example, long chain fatty amines used as corrosion inhibitors in steam condensate lines, according to GB 1 104 491. However, there is no disclosure or suggestion of its use as an asphalt emulsifier.

The asphalt residues (i.e. after curing of the emulsion) from slow-setting asphalt emulsions, especially slow-setting anionic emulsions, show poor adhesion to aggregates such as quartzite. The result is poor durability of road materials prepared using these emulsions.

The asphalt residues from slow-setting emulsions prepared from the polyamine polyoxide emulsifiers of the invention, however, show good adhesion and have particularly better adhesion than the residues derived from slow-setting cationic, anionic or nonionic emulsions prepared with the commonly-used nonylphenolethoxylate emulsifiers.

SUMMARY OF THE INVENTION

The present invention generally relates to a method of emulsifying asphalt using a novel asphalt emulsifier, an asphalt emulsion containing the novel asphalt emulsifier, and a cold mix of the asphalt emulsion containing the novel asphalt emulsifier. The method emulsifies a mixture of asphalt and water by adding an emulsifying effective amount of a novel asphalt emulsifier of at least one polyamine polyoxide. A polyamine (or polytertiaryamine) is defined herein as having more than one amine group, such as a di-, tri- or tetra-amine, etc. A polyoxide is defined herein as having more than one oxide group, such as a di-, tri- or tetra-oxide, etc.

The invention is especially useful in slow setting emulsions, since lower use levels are required when using the inventive emulsifier and the emulsifier can be used for either anionic or cationic slow setting emulsions depending on whether art acid or alkaline water phase is used. Both the cationic and anionic slow setting asphalt emulsions are of good quality and meet the requirements of slow setting grades at low use levels. The cured asphalt residue from emulsions made with the inventive emulsifier adhere better to aggregates than the asphalt residue from emulsions prepared with nonionic nonylphenolethoxylate emulsifiers.

Further, the emulsions of the present invention can be used for cold mix, where they exhibit advantages compared with a conventional cationic mixing grade emulsifier. Additionally, the inventive asphalt emulsifiers are compatible with both cationic and anionic co-emulsifiers, especially when combined with co-emulsifiers conventionally used for medium and rapid-setting emulsions. It is, thus, very economical to use the inventive asphalt emulsifiers, since lower use levels are required and it is only necessary to stock a single emulsifier for both anionic and cationic emulsions and for slow setting emulsions.

These and other objects of the invention are readily apparent from the following disclosure.

DETAILED DESCRIPTION OF THE INVENTION

The inventive process uses a polyamine polyoxide, preferably an amine polyoxide derived from a polyamine, more preferably a di-tertiary amine polyoxide, as an asphalt emulsifier or a co-emulsifier. A polyamine (or polytertiaryamine) is defined herein as having more than one amine group, such as a di-, tri- or tetra-amine, etc. A polyoxide is defined herein as having more than one oxide group, such as a di-, tri- or tetra-oxide, etc. It is not necessary that all the tertiary amine groups be oxidized. Preferably, all the tertiary amine groups are oxidized. More preferably, the polyamine polyoxides are formed by the oxidation of alkylated or oxyalkylated alkyl polyamines, preferably diamines. The emulsions formed using the inventive process meet the requirements for slow setting emulsions specified by the American Society for Testing and Materials (ASTM) and others, as demonstrated by the examples herein.

It is desirable that the novel asphalt emulsifier of the present invention be derived from an amine having the following formula I:

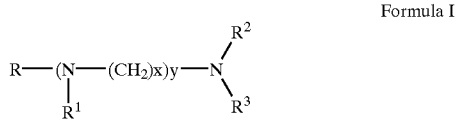

Formula I wherein R is a $C_8$–$C_{24}$ hydrocarbon radical, preferably a $C_8$–$C_{22}$ alkyl, alkenyl or mixture thereof; $R^1$, $R^2$ and $R^3$ are, independently, a $C_1$–$C_6$ alkyl or alkanol, preferably methyl, ethyl, ethanol, propanol, polyethoxyethanol, carboxyethyl or carboxymethyl in any combination, and more preferably methyl, ethanol, or polyethoxyethanol in any combination; x is an integer equal to or greater than 1; and y is an integer equal to or greater than 1.

It is also preferable that R is a $C_8$–$C_{18}$ hydrocarbon radical, including $C_{18}$ unsaturated alkyl chains or their mixtures. Additionally, it is preferred that R is derived from natural fats and oils, such as tallow, rapeseed(canola), soya, tall oil, etc., giving an alkyl chain range of $C_{12}$–$C_{18}$, including unsaturated alkyl chains, and, more preferably, R is tallow alkyl or hydrogenated tallow alkyl. It is also preferable that $R^1$, $R^2$, and $R^3$ are, independently, methyl, ethan-2-ol, propan-2-ol, polyoxyethylene, and are, more preferably, methyl or ethan-2-ol. Preferably, x=1–6, more preferably, x=2 or 3 and, even more preferably, x=3.

The novel asphalt emulsifier of the present invention is derived from a polyamine having formula I by oxidizing at least two of the nitrogens in the polyamine. Preferably, y 1–5, more preferably y 1–3, with y+1 indicating the number of oxidized nitrogens in the polyamine, if all the nitrogens are oxidized. Preferably, all the nitrogens are oxidized.

More preferably, the novel asphalt emulsifier of the present invention has the following formula II:

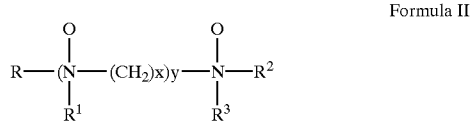

Formula II wherein R is a $C_8$–$C_{24}$ hydrocarbon radical, preferably a $C_8$–$C_{22}$ alkyl, alkenyl or mixture thereof; $R^1$, $R^2$ and $R^3$ are, independently, a $C_1$–$C_6$ alkyl or alkanol, preferably methyl, ethyl, ethanol, propanol, polyethoxyethanol, carboxyethyl or carboxymethyl in any combination, and more preferably methyl, ethanol, or polyethoxyethanol in any combination; x is an integer equal to or greater than 1; and y is an integer equal to or greater than 1, with y+1 indicating the number of oxidized nitrogens in the polyamine.

It is also preferable that R is a $C_8$–$C_{18}$ hydrocarbon radical, including $C_{18}$ unsaturated alkyl chains or their mixtures. Additionally, it is preferred that R is derived from natural fats and oils, such as tallow, rapeseed(canola), soya, fall oil, etc., giving an alkyl chain range of $C_{12}$–$C_{18}$, including unsaturated alkyl chains, and, more preferably, R is tallow alkyl or hydrogenated tallow alkyl. It is also preferable that $R^1$, $R^2$, and $R^3$ are, independently, methyl, ethan-2-ol, propan-2-ol, polyoxyethylene, and are, more preferably, methyl or ethan-2-ol. Preferably, x=1–6, more preferably, x=2 or 3 and, even more preferably, x=3. Preferably, y=1–5, more preferably Y=1–3, with y+1 indicating the number of oxidized nitrogens in the polyamine.

The best performing products are di-oxides prepared from di-amines with tertiary groups, such as $RN(CH_3)OCH_2CH_2CH_2N(CH_3)_2O$ or $RN(CH_2CH_2OH)OCH_2CH_2CH_2N(CH_2CH_2OH)_2O$, where R is tallow alkyl or hydrogenated tallow alkyl. For example, the best performing products include: N,N',N' trimethyl-N-tallow-1,3-diaminopropane, N, N' dioxides; N,N',N' trimethyl-N-hydrogenatedtallow-1,3-diaminopropane, N, N' dioxides; N,N',N' tris(2-hydroxyethyl)-N-tallow-1,3-diaminopropane, N, N' dioxides; and N,N',N' tris(2-hydroxyethyl)-N-hydrogenatedtallow-1,3-diaminopropane, N, N' dioxides.

Di-oxides prepared from ethoxylated alkyldiamines and polyamineoxides derived from ethoxylated polyamines are also within the scope of this invention.

The inventive emulsifiers can either be use alone or together with known co-emulsifiers or emulsion stabilizers.

The polyamine polyoxides used in the invention are prepared using any known standard method, such as, for example, mixing an amine, preferably a tertiary amine, sodium EDTA, isopropanol, water and hydrogen peroxide (1–1.3 moles of hydrogen peroxide for each tertiary amine group to be converted to an amine oxide group); and warming to 80° C. for 1 hour. The products described here were prepared at ca. 50% active matter. This method can be found in "Kinetics and Preparation of Amine Oxides", C. Joe Toney, F. E. Friedli, P. J. Frank, JAOCS Vol. 71, No. 7 July 1994. This entire publication is hereby incorporated by reference herein. Other oxidizing methods are known in the literature, e.g. the use of organic peroxides. Table 1 has examples of the polyamine polyoxides used in the invention and comparison examples thereof. In Table 1, the formula for the tertiary amine is given and each nitrogen is oxidized in the examples of the invention. The examples and comparison examples disclosed herein are frequently identified by the abbreviations Ex. and Comp. Ex., respectively.

TABLE 1

R(N (R1) (CH2)x)y N(R2)(R3)

| R | R1 | R2 | R3 | x | y | Name of tertiary amine | Amine oxide Example/ Comparison Ex. | No. of oxides (y + 1) |
|---|---|---|---|---|---|---|---|---|
| tallowalkyl | — | methyl | methyl | — | 0 | Armeen TMTD | Comp. Ex. 1 | 1 |
| cocoalkyl | — | Ethan-2-ol | Ethan-2-ol | — | 0 | Ethomeen C/12 | Comp. Ex. 2 | 1 |
| tallowalkyl | — | Ethan-2-ol | Ethan-2-ol | — | 0 | Ethomeen T/12 | Comp. Ex. 3 | 1 |
| tallowalkyl | methyl | methyl | methyl | 3 | 1 | Duomeen TTM | Example 1 | 2 |

TABLE 1-continued

R(N (R1) (CH2)x)y N(R2)(R3)

| R | R1 | R2 | R3 | x | y | Name of tertiary amine | Amine oxide Example/ Comparison Ex. | No. of oxides (y + 1) |
|---|---|---|---|---|---|---|---|---|
| tallowalkyl | Ethan-2-ol | Ethan-2-ol | Ethan-2-ol | 3 | 1 | Ethoduomeen T/13 | Example 2 | 2 |
| tallowalkyl | polyoxyethylene | polyoxyethylene | polyoxyethylene | 3 | 1 | Ethoduomeen T/25 | Example 3 | 2 |
| Hydrogenated tallowalkyl | Ethan-2-ol | Ethan-2-ol | Ethan-2-ol | 3 | 1 | Ethoduomeen HT/13 | Example 4 | 2 |
| Cocoalkyl | Ethan-2-ol | Ethan-2-ol | Ethan-2-ol | 3 | 1 | Ethoduomeen C/13 | Example 5 | 2 |

The inventive method of emulsifying asphalt in water uses an amount of polyamine polyoxide which is effective to emulsify asphalt in water. The effective amount is preferably about 0.3 to about 2.5%, more preferably about 0.5 to about 1.0%, by weight (as active matter). The inventive emulsion contains about 0.3 to about 2.5%, preferably about 0.5 to about 1.0%, by weight polyamine polyoxide emulsifier (as active matter), about 30–80% by weight asphalt, preferably about 55–70%, and the remainder water, except for small quantities of acid or alkali, e.g., HCl or NaOH, to adjust pH. Anionic emulsions are alkaline and cationic emulsions are acidic.

Other emulsifiers and emulsion additives can be included in the formulation to change the properties of the emulsion. These include thickeners, such as guar gum, stabilizers, such as aminolignin, quebracho, clays or lignin sulphonate, and additives, such as calcium chloride which is often used in cationic emulsions to control viscosity. Additives, such as polymers, can be added to either the asphalt phase or the soap phase to give improved properties to the residual asphalt. Solvents can be added to soften the asphalt.

Cold mixes are mixes of an emulsion of the above composition and aggregate (which may also include up to 100% reclaimed asphalt pavement), preferably about 2–25 parts of emulsion are present for every 100 parts of dry aggregate.

Asphalt emulsions are prepared by mixing the components at a temperature sufficient to soften the asphalt. Typically, the emulsifier, pH modifiers and additives (if any) are added to the water to prepare a 'soap' phase and this soap is then mixed with hot asphalt in a colloid mill (high shear mixer). Alternative methods are known in the asphalt emulsion industry.

The emulsions used in the examples were prepared as follows: The emulsifiers-were dissolved or dispersed in the water, the pH of the water was adjusted by the addition of hydrochloric acid (for cationic emulsions) or sodium hydroxide (for anionic emulsions), then this soap was heated to 50° C., before mixing with hot asphalt (130° C.) in a laboratory colloid mill. The emulsions were produced at 70–90° C., then cooled to room temperature.

The anionic and cationic emulsions were made using the examples of the amine oxides and comparison examples thereof which are shown in Table 1. Table 2 shows the results of the tests performed on the anionic emulsions and Table 3 shows the results for the cationic emulsions. The properties of the emulsions were compared using tests described in ASTM methods and elsewhere, in order to illustrate the advantages of the invention.

TABLE 2

| | Comp. Ex. 1 | Comp. Ex. 2 | Comp. Ex. 3 | Comp. Ex. 4 | Ex. 1 | Ex. 2 | Ex. 3 | Ex. 6 | ASTM Specification D977 SS-1 h |
|---|---|---|---|---|---|---|---|---|---|
| Emulsifier level % (Active matter) | 0.6 | 0.6 | 0.6 | 0.6 | 0.6 | 0.6 | 0.6 | 0.6 | |
| Appearance | broken | smooth | broken | Thick skin | smooth | smooth | Slight skin | smooth | |
| Asphalt Residue | N.D. | 61.1 | N.D. | 61.0 | 60.0 | 61.0 | 61.0 | 60.8 | 57 min |
| Viscosity Saybolt Furol 25° C. SFs | N.D. | 24 | N.D. | 18 | 24 | 25 | 20 | 23 | 20–100 |
| Sieve Test % | Broken >50 | 2.7 | Broken >50 | 0 | 0 | 0 | 0 | 0 | 0.1 max |
| Cement Mix Test % | N.D. | 9.4 | N.D. | 11.9 | 0 | 0.1 | 8.8 | 0 | 2 max |
| Sand Coating Test % | N.D. | 100 | N.D. | 100 | 100 | 100 | 100 | 100 | [100] |
| Sand Coating Test % | N.D. | 100 | N.D. | 0 | 100 | 100 | 0 | 100 | [50 min] |

*Comparison Example 4 is TDET ® N50 which is 50 mole ethoxylate of nonyl phenol supplied by Harcros Chemicals.
N.D. refers to no data.

TABLE 3

| | Comp. Ex. 1 | Comp. Ex. 2 | Comp. Ex. 3 | Comp. Ex. 4 | Ex. 1 | Ex. 2 | Ex. 3 | Ex. 5 | ASTM Specification D2397 CSS-1h |
|---|---|---|---|---|---|---|---|---|---|
| Emulsifier level % (Active matter) | 0.6 | 0.6 | 0.6 | 0.6 | 0.6 | 0.6 | 0.6 | 0.6 | |
| Appearance after manufacture | broken | smooth | smooth | Skin | smooth | smooth | Slight skin | Smooth | |
| Asphalt Residue | 61.4 | 61.6 | 61.2 | 61.2 | 60.7 | 61.1 | 61.8 | 61.2 | 57 min |

TABLE 3-continued

|  | Comp. Ex. 1 | Comp. Ex. 2 | Comp. Ex. 3 | Comp. Ex. 4 | Ex. 1 | Ex. 2 | Ex. 3 | Ex. 5 | ASTM Specification D2397 CSS-1h |
|---|---|---|---|---|---|---|---|---|---|
| Viscosity Saybolt Furol 25° C. SFs | N.D. | 24 | N.D. | 18 | 24 | 25 | 20 | 21 | 20–100 |
| Particle Charge test (8 mA) | pass | pass | pass | pass | pass | pass | pass | pass | positive |
| Sieve Test % | broken | 1.1 | broken | 0 | 0 | 0 | 0 | 0 | 0.1 max |
| Cement Mix Test % | N.D. | 27.2 | 96.7 | 0.2 | 0 | 0.1 | 0.8 | 0.1 | 2 max |
| Sand Coating Test Initial % | N.D. | 100 | 10 | 100 | 100 | 100 | 100 | 100 | [100] |
| Sand Coating Test After Boil % | N.D. | 95 | N.D. | 0 | 100 | 100 | 0 | 100 | 50 min* |

*only required if the particle charge test is failed.
N.D. refers to no data.

The test methods used on the emulsions in Tables 2 and 3 are summarized below:

Appearance: This is not specified in the ASTM standard. In this test series, any skin was removed before further testing. The presence of skin is shown by coagulated emulsion on the surface of the emulsion and is a sign of poor emulsion quality. Broken emulsion means that the emulsion has coagulated throughout its mass soon after production, or that it failed to emulsify at all. A smooth homogeneous emulsion indicates no obvious coagulation.

Asphalt residue: This refers to asphalt content by distillation. The emulsions did not contain any solvent, so a simplified method (evaporation on a hot plate) was used. The residue is the weight of material (mainly asphalt) remaining after boiling off the water and it is expressed as a percentage of the original weight of emulsion.

Viscosity: This is a measure of the consistency of the emulsion. It was measured with a standard flow cup. The units are Saybolt Furol seconds (SFs) which represent the time taken in seconds for 60 ml of emulsion to flow out of the standard cup.

Particle charge: The test distinguishes cationic emulsions from anionic emulsions. Electrodes are placed in the emulsion. A current (initially 8 mA) is applied for 30 minutes and then the electrodes are examined for deposits of asphalt. Cationic emulsions deposit on the cathode.

Sieve test: The emulsion is passed through a pre-weighed 840 micron sieve. Any large asphalt particles are retained and weighed. The results refer to the weight of particles retained on the sieve expressed as a percentage of the original weight of emulsion.

Cement Mix Test: The test distinguishes slow-setting emulsions from other asphalt emulsions. The emulsion is mixed with cement. Then, the mixture is passed through a pre-weighed No. 14 mesh sieve. The residue on the sieve is weighed. The result of the test is the weight in grams retained on the sieve obtained from 100 ml of emulsion (diluted to a nominal 55% residue content) after mixing with cement. The residue consists of coagulated emulsion and cement.

Sand Coating test: This test has been designed to distinguish cationic slow setting emulsions from other emulsions in the event that the emulsions do not pass the cement mix test. The test involves mixing a standard sand with emulsion, allowing the mix to cure on the bench, then immersing the mix in boiling water for 10 minutes and reexamining the coating. Here, it is used to visually estimate the coating ability of the emulsion and the adhesion of the cured emulsion film to quartz. For this reason, it has also been applied to anionic emulsions.

Emulsions giving good initial coating are suitable for mixing with aggregates. Emulsions giving good coating after immersion in boiling water will yield road materials showing good water resistance.

As demonstrated in Tables 2 and 3, the monoxides of Comp. Ex. 1, Comp. Ex. 2, and Comp. Ex. 3 provided emulsions of an inferior quality at the level of emulsifier employed (0.6%). These monoxide emulsions either broke or gave high sieve residues. The dioxides of Ex. 1, Ex. 2, and Ex. 3 of the invention gave good quality emulsions with low sieve residues.

None of the monoxides tested met the requirements of slow-setting cationic or anionic emulsions at this use level (0.6%). The dioxides of Ex. 1 and Ex. 2 met all the ASTM requirements for cationic and anionic emulsions at this emulsifier level (0.6%). The dioxide of Ex. 3 met the ASTM requirements for cationic, but not for anionic emulsions at this use level (0.6%).

The standard slow set emulsifier of Comp. Ex. 4 did not meet the requirements of either slow-setting cationic or anionic emulsions at this use level of 0.6%. Typical commercial slow-setting emulsifiers are used at 0.8–1.2% on an active basis. One of the advantages of the inventive use of polyamine polyoxides is their ability to make asphalt emulsions at low use levels.

The emulsions made with the diamine dioxides of Ex. 1 and Ex. 2 showed superior adhesion to the quartz sand than the standard slow set emulsifier Comp. Ex. 4. The performance of the dioxide of Ex. 3 was similar to the standard. Even the anionic emulsions gave good adhesion.

The inventive use of polyamine polyoxides for forming asphalt emulsions can be applied to cold mix formulations as well. Tests were conducted on a cold mix using, for example, a diamine dioxide having the following formula:

Example 7

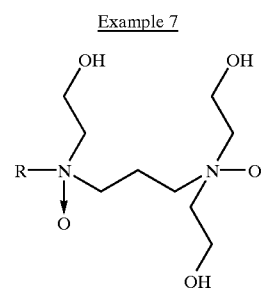

The dioxide can be made by any conventional method. It is generally formed in a solvent. When water is used as the solvent, the large amount of foam produced limits the concentration of the dioxide in the product to approximately 30%. The solution becomes too viscous at higher concentrations of amine oxide. Alternatively, the use of 2-propanol as the solvent permits the production of higher concentrations of amine oxides, approximately 50% or higher. However, the product is flammable with a flash point of about 12° C.

For example, when 2-propanol was used as the solvent to make the dioxide, 36.3 kg of the diamine of Example 7 and 34 kg 2-propanol were blended and warmed in the reactor at 30° C. Then, 7.3 kg hydrogen peroxide (35%) was added over 30 minutes and the reaction temperature was increased to about 70° C. The reaction mixture was allowed to react for 30 minutes and a sample was taken. The product had 50.5% diamine oxide and 0.7% unreacted diamine.

As a further example, when water was used as the solvent to make the dioxide, 180.5 g of diamine and 334 g water were warmed to about 30° C. Then, 98 g hydrogen peroxide (35% aqueous) was added dropwise and the reaction temperature was increased to about 70° C. The reaction mixture was allowed to react for 30 minutes and a sample was taken. The product had 30.1% diamine dioxide and 0.2% unreacted diamine.

The dioxide of Example 7 was used to prepare an asphalt emulsion which was subjected to cold paving (cold mix) and compared to a commercially available anionic emulsifier, Redicote EM 76 tallowtetramine (N-tallowalkyltripropylenetetra-amines) available from Akzo Nobel, which was used as a standard and is identified herein as Comparison Example 5. Table 4 shows the target recipe for each emulsion. Table 5 shows the properties of the emulsions as measured after manufacture. The relative performance of each emulsion when used in a cold mix is shown in Table 6 below.

TABLE 4

Emulsion (Cationic Mixing grade emulsion):

| Emulsifier | Comp. Ex. 5 (tallowtetramine) | Ex. 7 |
| --- | --- | --- |
| Emulsifier level (Active matter) % | 1.0 | 1.0 |
| Asphalt (B370 ex Nynas Sweden) | 62 | 62 |
| pH soap | 2.5 | 2.0 |
| Calcium chloride* | 0 | 0.1 |
| Water | To 100 | To 100 |

*used to control viscosity

TABLE 5

Emulsion Properties

| Emulsifier | Comp. Ex. 5 | Ex. 7 |
| --- | --- | --- |
| Use level (Active matter) % | 1.0 | 1.0 |
| Asphalt Content % | 64.6 | 63.1 |
| Particle Size (microns) | 4.5 | 2.5 |
| Viscosity STV (seconds) | 10 | 11 |
| Sieve residue % | 0.0 | 0.0 |
| Breaking Index | 142 | 138 |

The two emulsions in Table 4 were used in cold paving with a mix of semi-dense graded granite aggregate, 0/16mm from Telemark Norway, having 5.0% residual asphalt. Sufficient emulsion was used so that there was 5 parts by weight of asphalt for every 100 parts by weight of dry aggregate. Table 6 below shows the performance of each emulsion in cold paving.

TABLE 6

Performance tests on Mix

| Emulsifier | Comp. Ex. 5 | Ex. 7 |
| --- | --- | --- |
| Pre-wet water needed to get the right coating | 5 | 4 |
| Coating after mixing (coverage %) | 100 | 100 |
| Coating after rinsing (coverage %) | 90 | 100 |
| Coating after lay down (coverage %) | 100 | 100 |
| Power requirement of mixer at 70 ton/hour | 60 amp | 45 amp |
| Workability after 6 minutes | 162 | 146 |
| Workability after 15 minutes | 181 | 153 |
| Observation from paving crew | Stiff mix difficult to pave | OK |
| Cohesion 1 hr after compaction Nm | 50 | 52 |
| Cohesion 4 hr after compaction Nm | 93 | 92 |
| Cohesion 30 hrs after compaction Nm | 115 | 135 |
| Water resistance test (Boiling Stripping) % retained | 100 | 100 |

The test methods used on the cold mix in Table 6 are summarized below:

Particle Size

Determined with a Coulter LS230 particle sizer. This is the size of the asphalt droplets in the emulsion and is related to emulsion quality. Generally, a smaller particle size means better emulsion storage properties, viscosity, etc.

Viscosity STV

The STV "Standard Tar Viscometer" is an alternative flow cup method used in Europe.

Breaking Index

A method of determining the reactivity of cationic emulsions. Quartz filler is added to a 100 g emulsion until the mass cannot be mixed further. The breaking index is the weight in grams of the quartz filler required to completely break 100 g of emulsion. Rapid setting emulsions are defined as those giving values less than 100. The emulsions in this example were therefore slow or medium-setting. A high value means a more slow setting emulsion.

Pre-wet Water

Some water is added at the mix plant to improve coating and the consistency of the mix. Pre-wet water represents the parts by weight of water required to treat 100 parts by weight of dry aggregate. A low value is preferred and indicates the emulsion is more slow setting.

Coating After Mixing

The coverage of the aggregate surface is visually estimated as the mix comes out of the continuous mix plant. The results range from 0% ( uncoated) to 100% (fully coated).

Coating After Rinsing

The mix is washed with water in a test of 'rainfastness' of the coating and the coverage is again estimated visually. A 100% value is preferred, since it means the mix is resistant to rain.

Coating After Lay-down

Sometimes, the aggregate coating can be damaged by the transport and paving operation. The coating is estimated visually as the mixture is paved. One effect of poor coating at this stage will be that the roadway will not appear black.

Power Requirement

This is the power required by the mix plant. A high value indicates a 'stiff' material, difficult to mix and requiring more power to turn the mixer.

Workability

This is another measure of the 'stiffness' of the mix related to how easy it is to move the mix about and pass it through the paver. The method used was the Nynas Workability tester. The Nynas Workability tester is described in the following reference: Nynas Workability Test, B. Gustavsson and U. Lillbroanda, Eurasphalt & Eurobitume Congress 1996, Strassbourg France. The units are in Newtons. A high value implies a stiffer mix difficult to pave.

Paving Crew

The operators of the lay down equipment provided a subjective opinion of the properties of the mix.

Cohesion

This is a measure of the strength development in the mix. A spiked disc is driven into the surface of the roadway after compaction. The torque needed to turn the disc is measured. A high value means the surface of the roadway has developed more strength. The equipment used is described in the following reference: Asfaltutviklings—Prosjekteti Telemark, Publikasjon Nr 92, Statens Vegvesen, Vegdirektoratet ISSN 0803-6950 (in Norwegian). There is also some description of the equipment in: "*In—Plant Cold Recycling and Cold Mix in Sweden— Developments in Laboratory Testing*", Gunnar Hillgren, Alan James, Tomas Svenson and Thomas Wallin, 25$^{th}$ AEMA Annual meeting 1998, San Diego, Calif. The units are Nm (Newtons-meter).

Water Resistance (Stripping)

This is a measure of the water resistance of the road material. A sample of fully cured uncompacted mix is placed in boiling water for 5 minutes and the coating is estimated visually. The test shows the effect of water on the cured asphalt residue left on the aggregate surface. A loss in coating by the effect of water ('stripping') shows poor adhesion between asphalt and aggregate and suggests that the roadway will have poor durability.

As demonstrated in Tables 4–6, the dioxide of Ex. 7 made an emulsion with a slightly better particle size and of otherwise similar good quality to the standard. Additionally, the emulsion of Ex. 7 mixed more easily with the aggregate than did the emulsion made with the standard cationic emulsifier. Further, the mix made with Ex. 7 was more workable (less stiff), but had similar cohesion building and adhesion properties to the standard.

The inventive concept is further explained by the foregoing claims, but is not limited thereby.

What is claimed is:

1. A method of emulsifying asphalt in water comprising adding to a mixture of asphalt and water an emulsifying effective amount of at least one polyamine polyoxide.

2. The method of claim 1, wherein the polyamine polyoxide is a diamine dioxide.

3. The method of claim 1, wherein the polyamine polyoxide is ethoxylated.

4. The method of claim 1, wherein the emulsion formed is anionic, cationic and/or slow setting.

5. The method of claim 1, wherein the polyamine polyoxide is formed by the oxidation of at least two nitrogens of the polyamine of the following formula I:

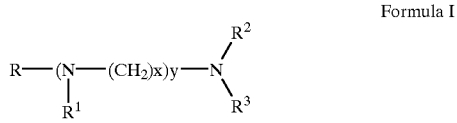

Formula I wherein R is a $C_8$–$C_{24}$ alkyl, alkenyl or mixture thereof; $R^1$, $R^2$ and $R^3$ are, independently, a $C_1$–$C_6$ alkyl or alkanol, polyethoxyethanol, carboxyethyl or carboxymethyl; x=1–6; and y is an integer greater than or equal to 1.

6. The method of claim 5, wherein R is tallow alkyl or hydrogenated tallow alkyl; $R^1$, $R^2$ and $R^3$ are, independently, methyl, ethyl, ethanol, propanol, polyethoxyethanol, carboxyethyl or carboxymethyl in any combination; and x=2 or 3.

7. The method of claim 5, wherein the polyamine polyoxide is $RN(CH_3)OCH_2CH_2CH_2N(CH_3)_2O$ or $RN(CH_2CH_2OH)OCH_2CH_2N(CH_2CH_2OH)_2O$, where R is tallow alkyl or hydrogenated tallow alkyl and x=3.

8. The method of claim 1, wherein the amount of polyamine polyoxide ranges from about 0.3% to about 2.5% by weight of the mixture.

9. The method of claim 8, wherein the amount of polyamine polyoxide ranges from about 0.5% to about 1.0% by weight of the mixture.

10. The method of claim 1, wherein the polyamine polyoxide has the following formula II:

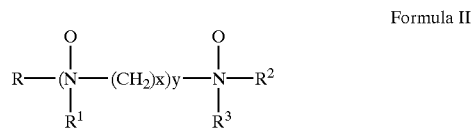

Formula II wherein R is a $C_8$–$C_{24}$ alkyl, alkenyl or mixture thereof; $R^1$, $R^2$ and $R^3$ are, independently, a $C_1$–$C_6$ alkyl or alkanol, polyethoxyethanol, carboxyethyl or carboxymethyl; x=2 or 3; and y is an integer greater than or equal to 1.

11. The method of claim 1, wherein the polyamine polyoxide is selected from the group consisting of N,N',N' trimethyl-N-tallow-1,3-diaminopropane, N,N' dioxides; N,N',N' trimethyl-N-hydrogenated tallow-1,3-diaminopropane, N,N' dioxides; N,N',N' tris(2-hydroxyethyl)-N-tallow-1,3-diaminopropane, N,N' dioxides; and N,N',N' tris(2-hydroxyethyl)-N-hydrogenated tallow-1,3-diaminopropane, N,N' dioxides.

12. The method of claim 1, wherein the polyamine polyoxide is formed by the oxidation of alkylated or oxyalkylated alkyl polyamines.

13. An emulsion of asphalt, water and at least one polyamine polyoxide effective to emulsify the asphalt in the water; the polyamine polyoxide being present in an amount effective to emulsify the asphalt in the water; and the polyamine polyoxide being formed by the oxidation of at least two nitrogens of the polyamine of the following formula I;

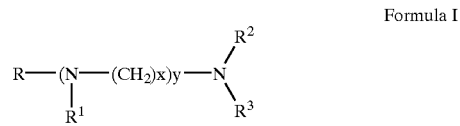

Formula I wherein R is tallow or hydrogenated tallow; $R^1$, $R^2$ and $R^3$ are, independently, methyl, ethyl, ethanol, propanol, polyethoxyethanol, carboxyethyl or carboxymethyl in any combination; x=2 or 3; and y is an integer greater than or equal to 1.

14. The emulsion of claim 13, wherein the emulsion is cationic, anionic and/or slow setting.

15. The emulsion of claim 13, wherein the effective amount of polyamine polyoxide ranges from about 0.3% to about 2.5% by weight of the mixture.

16. The emulsion of claim 15, wherein the effective amount of polyamine polyoxide ranges from about 0.5% to about 1.0% by weight of the mixture.

17. A cold mix comprising the emulsion of claim 13, and aggregate.

18. The cold mix of claim 17, wherein the emulsion is present in an amount of about 2 to about 25% of the weight of the aggregate when the aggregate is dry.

19. An emulsion of asphalt, water and at least one polyamine polyoxide effective to emulsify the asphalt in the water; the polyamine polyoxide being present in an amount effective to emulsify the asphalt in the water; the polyamine polyoxide being formed by the oxidation of at least two nitrogens of the polyamine of the following formula I:

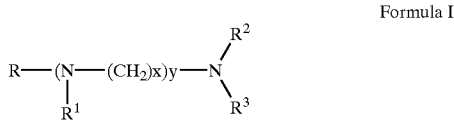

Formula I wherein R is a $C_8-C_{24}$ alkyl, alkenyl or mixture thereof; $R^1$, $R^2$ and $R^3$ are, independently, a $C_1-C_6$ alkyl or alkanol, polyethoxyethanol, carboxyethyl or carboxymethyl; x=1–6; and y is an integer greater than or equal to 1; and the polyamine polyoxide being $RN(CH_3)OCH_2CH_2CH_2N(CH_3)_2O$ or $RN(CH_2CH_2OH)OCH_2CH_2CH_2N(CH_2CH_2OH)_2O$, where R is tallow alkyl or hydrogenated tallow alkyl.

20. The emulsion of claim 19, wherein the emulsion is cationic, anionic and/or slow setting.

21. The emulsion of claim 19, wherein the effective amount of polyamine polyoxide ranges from about 0.3% to about 2.5% by weight of the mixture.

22. The emulsion of claim 21, wherein the effective amount of polyamine polyoxide ranges from about 0.5% to about 1.0% by weight of the mixture.

23. A cold mix comprising the emulsion of claim 19 and aggregate.

24. The cold mix of claim 23, wherein the emulsion is present in an amount of about 2 to about 25% of the weight of the aggregate when the aggregate is dry.

25. An emulsion of asphalt, water and at least one polyamine polyoxide effective to emulsify the asphalt in the water; the polyamine polyoxide being present in an amount effective to emulsify the asphalt in the water, and the polyamine polyoxide being selected from the group consisting of N,N',N' trimethyl-N-tallow-1,3-diaminopropane, N,N' dioxides; N,N',N' trimethyl-N-hydrogenated tallow-1, 3-diaminopropane, N,N' dioxides; N,N'N' tris(2-hydroxyethyl)-N-tallow-1,3-diaminopropane, N,N' dioxides; and N,N',N' tris(2-hydroxyethyl)-N-hydrogenated tallow-$_{1,3}$-diaminopropane, N,N' dioxides.

26. The emulsion of claim 25 wherein the emulsion is cationic, anionic and/or slow setting.

27. The emulsion of claim 25, wherein the effective amount of polyamine polyoxide ranges from about 0.3% to about 2.5% by weight of the mixture.

28. The emulsion of claim 27, wherein the effective amount of polyamine polyoxide ranges from about 0.5% to about 1.0% by weight of the mixture.

29. A cold mix comprising the emulsion of claim 25 and aggregate.

30. The cold mix of claim 29, wherein the emulsion is present in an amount of about 2 to about 25% of the weight of the aggregate when the aggregate is dry.

* * * * *

UNITED STATES PATENT AND TRADEMARK OFFICE
CERTIFICATE OF CORRECTION

PATENT NO. : 6,494,944 B1
DATED : December 17, 2002
INVENTOR(S) : Wates et al.

It is certified that error appears in the above-identified patent and that said Letters Patent is hereby corrected as shown below:

Column 12,
Line 63, "13, and" should read -- 13, and --

Column 13,
Line 14, "tallow-$_{1,3}$-diaminopropane," should read -- tallow-1,3-diaminopropane, --

Signed and Sealed this

Seventh Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,494,944 B1
DATED : December 17, 2002
INVENTOR(S) : Wates et al.

It is certified that error appears in the above-identified patent and that said Letters Patent is hereby corrected as shown below:

Column 12,
Line 63, "13, and" should read -- 13 and --

Column 13,
Line 14, "tallow-$_{1,3}$-diaminopropane," should read -- tallow-1,3-diaminopropane, --

This certificate supersedes Certificate of Correction issued September 7, 2004.

Signed and Sealed this

Twenty-eighth Day of December, 2004

JON W. DUDAS
*Director of the United States Patent and Trademark Office*